United States Patent
Zhang et al.

(10) Patent No.: US 7,833,660 B1
(45) Date of Patent: Nov. 16, 2010

(54) FLUOROHALOBORATE SALTS, SYNTHESIS AND USE THEREOF

(75) Inventors: Shengshui Zhang, Olney, MD (US); Conrad Xu, North Potomac, MD (US); T. Richard Jow, Potomac, MD (US)

(73) Assignee: The United States of America as represented by the Secretary of the Army, Washington, DC (US)

(*) Notice: Subject to any disclaimer, the term of this patent is extended or adjusted under 35 U.S.C. 154(b) by 1104 days.

(21) Appl. No.: 11/518,747

(22) Filed: Sep. 7, 2006

(51) Int. Cl.
*H01M 6/04* (2006.01)
*H01G 9/02* (2006.01)

(52) U.S. Cl. .................... 429/188; 252/62.2

(58) Field of Classification Search ............. 429/188
See application file for complete search history.

(56) References Cited

U.S. PATENT DOCUMENTS

| | | | |
|---|---|---|---|
| 4,026,905 A | 5/1977 | Cohen et al. | |
| 4,209,465 A | 6/1980 | Austin et al. | |
| 4,313,843 A | 2/1982 | Bollyky et al. | |
| 4,496,730 A | 1/1985 | Chen et al. | |
| 4,505,997 A | 3/1985 | Armand et al. | |
| 4,552,825 A | 11/1985 | Chen et al. | |
| 4,885,228 A | 12/1989 | Inagaki et al. | |
| 4,900,854 A | 2/1990 | Winterton et al. | |
| 5,273,840 A | 12/1993 | Dominey | |
| 5,395,862 A | 3/1995 | Neckers et al. | |
| 5,397,675 A | 3/1995 | Arimatsu et al. | |
| 5,508,130 A | 4/1996 | Golovin | |
| 5,514,493 A | 5/1996 | Waddell et al. | |
| 5,623,023 A | 4/1997 | Nishikubo | |
| 5,641,577 A | 6/1997 | Naruse et al. | |

(Continued)

FOREIGN PATENT DOCUMENTS

JP 63215723 A 9/1988

(Continued)

OTHER PUBLICATIONS

Minkwitz, R., R. Nass, and H. Pruet. "Dimethyl-N-Halogenamine, Ihre Ammoniumsalze Und Bortrihalogenid-Addukte." Zeitschrift Fuer Anorganische Und Allgemeine Chemie 546 (1987): 99-106.*

(Continued)

*Primary Examiner*—Dah-Wei D Yuan
*Assistant Examiner*—Stephan Essex
(74) *Attorney, Agent, or Firm*—William W. Randolph; Avrom David Spevack

(57) ABSTRACT

A composition is provided as a salt having the formula $MBF_3X$ where M is an alkali metal cation and X is the halide fluoride, bromide or iodide. A lithium salt has several characteristics making the composition well suited for inclusion within a lithium-ion battery. A process for forming an alkali metal trifluorohaloborate salt includes the preparation of a boron trifluoride etherate in an organic solvent. An alkali metal halide salt where the halide is chloride, bromide or iodide is suspended in the solution and reacted with boron trifluoride etherate to form an alkali metal trifluorohaloborate. The alkali metal trifluorohaloborate so produced is collected as a solid from the solution. The process is simple and yields alkali metal trifluorohaloborate of sufficient purity to be used directly in battery applications.

22 Claims, 3 Drawing Sheets

U.S. PATENT DOCUMENTS

| | | |
|---|---|---|
| 5,652,072 A | 7/1997 | Lamanna et al. |
| 5,683,832 A | 11/1997 | Bonhote et al. |
| 5,827,602 A | 10/1998 | Koch et al. |
| 5,874,616 A | 2/1999 | Howells et al. |
| 5,916,475 A | 6/1999 | Michot et al. |
| 5,972,544 A | 10/1999 | Carr et al. |
| 6,010,806 A | 1/2000 | Yokoyama et al. |
| 6,063,467 A | 5/2000 | Kanno |
| 6,133,431 A | 10/2000 | Yasuda et al. |
| 6,185,089 B1 | 2/2001 | Mita et al. |
| 6,210,830 B1 | 4/2001 | Sartori et al. |
| 6,315,918 B1 | 11/2001 | Mita et al. |
| 6,319,428 B1 | 11/2001 | Michot et al. |
| 6,331,204 B1 | 12/2001 | Carr et al. |
| 6,344,497 B1 | 2/2002 | Meyrick et al. |
| 6,365,301 B1 | 4/2002 | Michot et al. |
| 6,423,454 B1 | 7/2002 | Heider et al. |
| 6,429,587 B1 | 8/2002 | Sugimachi et al. |
| 6,522,463 B1 | 2/2003 | Shimomura et al. |
| 6,559,222 B1 | 5/2003 | Rooney et al. |
| 6,576,627 B1 | 6/2003 | Fushihara et al. |
| 2002/0033661 A1 | 3/2002 | Sugimachi et al. |
| 2002/0153253 A1 | 10/2002 | Nishino et al. |
| 2002/0183204 A1 | 12/2002 | Nomura et al. |
| 2003/0108800 A1 | 6/2003 | Barbarich |
| 2003/0119787 A1 | 6/2003 | Fushihara et al. |
| 2003/0128264 A1 | 7/2003 | Ishikawa et al. |

FOREIGN PATENT DOCUMENTS

| | | |
|---|---|---|
| JP | 10337959 A | 12/1998 |

OTHER PUBLICATIONS

Hunt, Robin L., and Bruce S. Ault. "Spectroscopic Influences of Ion Pairing: Infrared Matrix-isolation Spectra of the Metal Tetrafluoroborate (M+BF4-) Ion Pair and Its Chlorine-fluorine Analogs." Spectrochimica Acta, Part A: Molecular and Biomolecular Spectroscopy 37A.2 (1981): 63-69.*

Zhang et al. Low-temperature performance of Li-ion cells with a LiBF4-based electrolyte, J Solid State Electrochem (2003) 7:147-151.

* cited by examiner

FLUOROHALOBORATE SALTS, SYNTHESIS AND USE THEREOF

GOVERNMENT INTEREST

The invention described herein may be manufactured, used, and licensed by or for the United States Government.

FIELD OF THE INVENTION

This invention in general relates to fluorohaloborates and in particular to an organic synthesis for and use of high pure trifluoroborates in non-aqueous electrochemical cells.

BACKGROUND OF THE INVENTION

The development of rechargeable alkali metal-ion batteries requires use of high quality salts. These salts should meet such requirements such as: providing high ionic conductivity over wide temperature range; being electrochemically stable relative to cathode and anode materials, especially at the fully charged state; being capable of passivating current collector material, such as aluminum, of the cathode at high potentials; being able to assist the formation of a stable solid electrolyte interphase (SEI) with carbonaceous anode materials; having high solubility at low temperatures; and being thermally stable at high temperatures. Among many commercially available lithium salts, only few are found to satisfy the above requirements. These salts include lithium hexafluorophosphate ($LiPF_6$), lithium perfluoroalkyl-substituted fluorophosphates, as detailed in U.S. Pat. Nos. 6,210,830 and 6,423,454, lithium tetrafluoroborate ($LiBF_4$), and recently developed lithium bis(oxalate)borate (LiBOB), as detailed in Patents DE 19829030 C1 and U.S. Pat. No. 6,506,516. It is noted that all these salts either contain phosphorus or contain boron. Extensive spectroscopic analyses have revealed that the SEI on the surface of carbonaceous anode in lithium-ion batteries must contain molecular moieties of halogen and phosphorus, or halogen and boron. These analyses suggest that the unique properties of these salts in lithium-ion batteries are associated with the presence of phosphorus and boron.

$LiBF_4$ has been used as a conducting salt for electrolytes in both primary cells and rechargeable cells. The electrolytes in these batteries are non-aqueous solutions of $LiBF_4$ in organic solvent, e.g. in dimethyl carbonate, diethyl carbonate, ethylmethyl carbonate, ethylene carbonate, propylene carbonate, other carbonates, or mixtures of the solvents mentioned. However, $LiBF_4$ is relatively inefficient in facilitating the formation of stable SEI on the surface of graphite. Additionally, an electrolytic solution containing $LiBF_4$ salt has relatively low ionic conductivity because of the tight ion pairing between $Li^+$ cations and $BF_4^-$ anions.

Several prior art references teach methods for preparing highly pure $LiBF_4$ by a means of the reaction of $BF_3$ and LiF in non-aqueous media. These have all met with limited success.

SU 1013405 describes the preparation of $LiBF_4$ in tetrahydrofuran (THF) by reacting LiF with $BF_3$ in yields of from 86 to 89%. The product is isolated by concentrating the THF solution. This generally gives a product containing considerable amounts of residual THF. To remove residual THF, drying in vacuum at from 70 to 80° C. for from 10 to 15 hours is proposed.

JP-A 56145113 describes a process for preparing $LiBF_4$ by reacting LiF with $BF_3$ in non-aqueous organic solvents in which $LiBF_4$ has good solubility and which can form complexes with $BF_3$. Non-aqueous organic solvents mentioned are tetrahydrofuran, dimethoxyethane, ethyl acetate and propylene carbonate. After the reaction of LiF with $BF_3$, impurities are filtered off. $LiBF_4$ is crystallized from the filtrate by saturating the solution with $BF_3$. With the solvent, $BF_3$ forms a complex in which $LiBF_4$ has low solubility, and the product crystallizes.

U.S. Pat. No. 6,537,512 describes a method for preparing $LiBF_4$ by reacting $BF_3$ etherate and suspending LiF in dimethyl ether solution to produce $LiBF_4$. As the solubility of $LiBF_4$ is low in dimethyl ether, the formed $LiBF_4$ can be easily separated off by traditional filtering methods. However, LiF being insoluble in dimethyl ether is present in the prepared $LiBF_4$.

Lee et al. describes in Journal of the Electrochemistry Society 145(8), 2813-2818 (1998) that LiCl is more soluble in dimethyl ether than LiF, and that LiCl dissolved in the solution can easily form highly soluble 1:1 mole ratio complex with a variety of boron-based organic anion acceptors. No effort is reported as to the separation of resulting complex as a pure salt nor is $BF_3$ described as the anion acceptor.

In view of the failure of any known salt to adequately satisfy the requirements for an alkali metal-ion battery salt, there exists a need for a new salt produced by a method of production that yields a high purity salt in scaleable quantities.

SUMMARY OF THE INVENTION

A composition is provided as a salt having the formula $MBF_{4-n}X_n$ where M is an alkali metal cation or a quaternary organic ammonium cation; n=1, 2, or 3; and X is the halide chloride, bromide or iodide. A lithium salt has several characteristics making the composition well suited for inclusion within a lithium-ion battery.

A process for forming an alkali metal fluorohaloborate salt includes the preparation of a boron trifluoride etherate in an organic solvent. An alkali metal halide salt or a quaternary organic ammonium halide salt where the halide is chloride, bromide or iodide is suspended in the solution and reacted with boron trifluoride etherate to form an alkali metal or quaternary ammonium fluorohaloborate. The fluorohaloborate so produced is collected as a solid from the solution. The process yields fluorohaloborates of sufficient purity to be used directly in battery applications.

DESCRIPTION OF THE PREFERRED EMBODIMENTS

Figure 1:
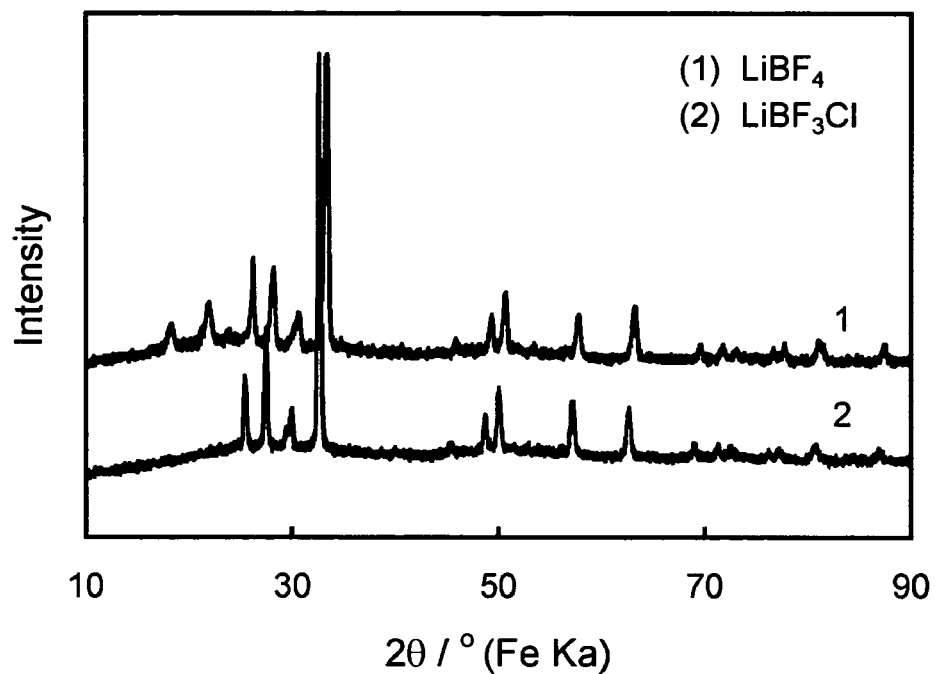
FIG. 1 is a plot comparing X-ray diffraction patterns of $LiBF_3Cl$ and the prior art $LiBF_4$.

The present invention has utility in non-aqueous electrochemical cells. The inventive composition has the formula $$MBF_{4-n}X_n \quad (I)$$

where M is $R_1R_2R_3R_4N^+$, an alkali metal cation of lithium, sodium, potassium or cesium; n is an integer 1, 2, or 3; X is a halide chloride, bromide or iodide; and each of $R_1$, $R_2$, $R_3$ and $R_4$ is independently $C_1$-$C_8$ alkyl. The inventive composition has the attribute of forming $X_2$ upon exposure to oxygen. Within a lithium-ion battery oxygen is released during overcharge. This inventive attribute has the advantage of protecting a non-aqueous electrolyte battery from cathodic overcharge exotherms. Additionally, $X_2$ in electrolyte solution is reducible to $X^-$ during a subsequent discharge process to return the cell to a stable state. Additionally, it is appreciated that an inventive composition has applications as a synthetic reagent operative as an oxygen getter and halogen X donor.

A typical process for producing an inventive fluorohaloborate (I) includes the preparation of a boron trifluoride etherate solution in an organic solvent. To this solution a dry salt of the formula MX is added in appropriate stoichiometry. For n=1, 2, or 3 the reaction $$nMX + BF_3 \rightarrow MBF_{4-n}X_n + (n-1)MF \quad (II)$$

or, for n=3

$$BX_3 + MF \rightarrow MBFX_3 \quad (III)$$

where M, X and n are as defined with respect to (I). The salt and the boron trifluoride etherate solutions are preferably prepared such that water is absent or at least present only in trace amounts.

It is appreciated that salts MX are soluble in neat boron trifluoride organic adduct complex and as such are usable absent an organic solvent. Suspension of the slightly soluble salt MX or MF in neat boron trifluoride or $BX_3$ organic adduct complex or a boron the organic adduct complex solution is reacted to yield the inventive alkali metal fluorohaloborate. Typical reaction temperatures range from 0-150° C. The resulting inventive alkali metal fluorohaloborate has considerable solubility in a solution of, or neat boron trifluoride or $BX_3$ organic adduct complex. A purified form of the inventive composition is obtained by filtering to remove unreacted salt MX or MF and then concentrating the solution or neat boron trifluoride or $BX_3$ organic adduct complex to crystallize the inventive composition. Subsequent purification is optionally performed by techniques conventional to the art illustratively including solvent extraction and recrystallization.

An inventive fluorohaloborate synthetic reaction is generally carried out with heating, preferably heating to solvent reflux. The reaction time depends on the temperature selected. The reaction is generally allowed to continue for from 4 to 10 hours. However, it is appreciated that reaction at room temperature or below occurs with a corresponding increase in reaction time. More preferably, the reaction is carried out in a pressurized vessel and at elevated temperatures from 80 to 110° C. Excess MX or MF is separated by filtering with the resulting solution being concentrated. The concentrated solution is added to diethyl ether in which the composition (I) has low solubility, such that the composition (I) is precipitated, filtered, and washed with diethyl ether. The proportion of MX or MF in the final product (I) is typically less than 2% by weight, preferably less than 1%. The final product also is characterized by low proportions of acid impurities, low moisture, and low proportions of heavy metals.

A boron trifluoride or $BX_3$ organic adduct complex such as $BF_3$ etherate or $BCl_3$ etherate is readily prepared by dissolution of pure boron trifluoride or boron trichloride complex with a solvent or alternatively produced by bubbling gaseous $BF_3$ or $BCl_3$ into an organic solvent. A boron trifluoride or $BX_3$ organic adduct complex operative herein includes a coordinate covalent bond between boron trifluoride or $BX_3$ and an aprotic heteroatom containing species such that the heteroatom containing species forms a suitable leaving group after reaction. Preferably, the heteroatom containing species is volatile under reaction conditions between a complex and a metal alkoxy or an ester. Heteroatom containing species that forms a portion of a boron trifluoride complex according to the present invention illustratively include: ($C_1$-$C_6$ alkyl)-O-($C_1$-$C_6$ alkyl), tetrahydrofuran, a $C_1$-$C_6$ dialkoxy of a $C_2$-$C_6$ alkane, and ($C_1$-$C_6$ alkyl)-S-($C_1$-$C_6$ alkyl). Specific examples of heteroatom containing species include diethyl ether, tetrahydrofuran, diethoxyethane and dimethylthioether.

The organic solvent is selected to itself form a complex with boron trifluoride or $BX_3$ or solubilize such a complex. The solvent is a single or a mixture of aprotic solvents where aprotic solvents operative herein illustratively include dimethylcarbonate ($C_1$-$C_6$ alkyl)-OC(O)-O-($C_1$-$C_6$ alkyl), a $C_2$-$C_8$ alkaline carbonate, a $C_1$-$C_6$ dialkoxy of a $C_2$-$C_6$ alkane, a $C_1$-$C_6$ ester of a $C_2$-$C_8$ carboxylic acid, a $C_1$-$C_6$ alkyl tetrahydrofuran and mixtures thereof. Specific examples of aprotic solvents include dimethyl carbonate, diethyl carbonate, ethyl methyl carbonate, methyl propyl carbonate, propylene carbonate, ethylene carbonate, 1,2-dimethoxyethane, 1,2-diethoxyethane, methyl acetate, gamma-butyrolactone, ethyl acetate, methyl propionate, ethyl propionate, methyl butyrate, ethyl butyrate, dimethyl sulfoxides, dioxolane, sulfolane, 1-methyl-2-pyrrolidinone, cetonitrile, acrylonitrile, tetrahydrofuran, 2-methyltetrahydrofuran and mixtures thereof. Preferably, the solvent is selected to dissolve the salt MX or MF. The volume ratio of the solvent to boron trifluoride organic adduct complex is typically from 1 to 20 and preferably from 1 to 10.

In the instance when the inventive compound is $LiBF_3Cl$, dimethoxyethane represents a preferred solvent in which hydrous LiCl is added to dimethoxyethane and stirred to promote LiCl dissolution. Completely dried LiCl is added to dimethoxyethane and stirred to promote its dissolution. The excess LiCl is suspended in the solution. Optionally LiCl is suspended in dimethoxyethane and this suspension is added to a neat $BF_3$ organic adduct complex or to a solution of $BF_3$ organic adduct complex, or $BF_3$ gas is bubbled into the suspension. The amount of $BF_3$ organic adduct complex used is typically a stoichiometric equivalent to that of LiCl. Preferably, a small excess of $BF_3$ organic adduct complex is present. More preferably, the molar ratio of $BF_3$ organic adduct complex to LiCl is between 0.80 to 1.2 inclusive. The molar ratio of $BF_3$ organic adduct complex to LiCl is most preferably from 1 to 1.05 inclusive. For $MBF_2X_2$ and $MBFX_3$ the molar ratios are double and triple, respectively, those detailed above for $LiBF_3Cl$ with MX replacing LiCl.

A particular advantage of the inventive composition (I) in non-aqueous electrolyte batteries is the propensity to reduce gas generation at the cathode during overcharging. While this advantage is further illustrated with respect to $LiBF_3Cl$ in a lithium-ion battery, it is appreciated that this advantageous property is found throughout the group of composition (I). When a cathode is overcharged, oxygen species having high oxidative potential are released from transition metal oxide cathodes. The exothermic release of oxidative oxygen species creates the potential for a thermal runaway reaction.

Propensity of sodium ion batteries towards thermal runaway reactions and the flammability of molten sodium upon cell failure are largely responsible for the limited acceptance of such batteries. $NaBF_{4-n}X_n$ where n is 1, 2 or 3 and represents an attractive electrolyte in sodium cells.

In the context of lithium-ion batteries, $LiBF_{4-n}X_n$ where n is 1, 2 or 3 reacts with oxygen species associated with cathode overcharge to create a less reactive and more soluble chlorine $Cl_2$, $Br_2$ or $I_2$ in the electrolyte solution that are amenable to reversible reduction to halide ions during a subsequent discharge process. In this way, $LiBF_{4-n}X_n$ serves as an electronic shuttle species to protect a battery cathode from overcharge. A greater safety margin thus results from a conventional non-aqueous electrolyte battery containing an inventive fluorohaloborate. As a result, an inventive fluorohaloborate (I) improves the performance of electrochemical devices such as battery cells, capacitors, double layer capacitors, electrolytic cells, and supercapacitors. A carbon/inventive electrolyte borate (I)/carbon double layer capacitor is a particularly preferred double layer capacitor according to the present invention.

An inventive halogenated borate is solvated to create an operative electrolyte. The solvent is a single or preferably a mixture of aprotic solvents where aprotic solvents operative herein illustratively include dimethylcarbonate, $(C_1-C_6$ alkyl)-OC(O)—O—$(C_1-C_6$ alkyl), a $C_2-C_8$ alkaline carbonate, a $C_1-C_6$ dialkoxy of a $C_2-C_6$ alkane, a $C_1-C_6$ ester of a $C_2-C_8$ carboxylic acid, a $C_1-C_6$ alkyl tetrahydrofurans and mixtures thereof. Specific examples of aprotic solvents include dimethyl carbonate, diethyl carbonate, ethyl methyl carbonate, methyl propyl carbonate, propylene carbonate, ethylene carbonate, 1,2-dimethoxyethane, 1,2-diethoxyethane, methyl acetate, gamma-butyrolactone, ethyl acetate, methyl propionate, ethyl propionate, methyl butyrate, ethyl butyrate, dimethyl sulfoxides, dioxolane, sulfolane, 1-methyl-2-pyrrolidinone, cetonitrile, acrylonitrile, tetrahydrofuran, 2-methyltetrahydrofuran and mixtures thereof. According to the present invention, electrolyte solvent is a mixture of at least one and preferably three solvents that function synergistically to solubilize an inventive halogenated borate, promote thermal stability, and enhance ionic conductivity. Preferably, at least one of the solvents is an alkaline carbonate and a second solvent is $(C_1-C_6$ alkyl)-OC(O)—(O)—$(C_1-C_6$ alkyl). More preferably, the alkaline carbonate is a $C_2-C_6$ alkaline carbonate. Still more preferably, a lactone is present in the solvent mixture. Most preferably, the weight ratio of alkaline carbonate to $(C_1-C_6$ alkyl)-OC(O)—O—$(C_1-C_6$ alkyl) is from 0.1 to 10:1.

EXAMPLES

The present invention is further detailed by way of the following non-limiting examples. These examples are not intended to limit the scope of the present invention, but rather to detail specific aspects thereof.

Example 1

Synthesis of $LiBF_3Cl$

In a glove-box having a moisture level less than 20 ppm, 4.26 g (0.03 mol) of $BF_3$ etherate is diluted with 20 ml of dimethoxyethane and placed in a Teflon reactor, to which 1.27 g (0.03 mol) of anhydrous LiCl is added with stirring. Small bubbles of diethyl ether immediately appear on the surface of LiCl crystals, and the LiCl starts to dissolve. The mixture is stirred for 16 hours at 40° C. Any residual LiCl is filtered out. The filtrate is concentrated under reduced pressure to 6 ml, cooled to 20° C., and poured into 30 ml diethyl ether. The solid $LiBF_3Cl$ precipitate is filtered and washed with diethyl ether, followed by drying for 1 hour in a flow of nitrogen and then at 100-110° C. under vacuum for 8 hours. A total of 2.61 g (79% of theory) of $LiBF_3Cl$ is obtained.

Crystallographic structure of the salt prepared above is characterized by X-ray diffraction with FeKa radiation. FIG. 1 compares X-ray diffraction patterns of inventive $LiBF_3Cl$ and prior art $LiBF_4$. It is indicated that these two salts have very similar crystallographic structure. However, substitution of chloride for one fluoride in $LiBF_4$ results in all diffraction peaks shifting slightly lower in 2θ and two peaks at 18 and 22 degree disappeared. These results suggest that $LiBF_3Cl$ has larger cell parameters than $LiBF_4$. NMR spectra are analyzed using D6-acetone as the solvent.

$^{19}$F-NMR: δ=156.05 ppm vs. 152.63 ppm of $LiBF_4$ (referenced to Freon-12)

$^{11}$B-NMR: δ=0.85 ppm vs. 1.24 ppm of $LiBF_4$ (referenced to $H_3BO_3$)

Example 2

Synthesis of $NaBF_3Br$

The procedure of Example 1 is repeated with the substitution of 3.09 g (0.03 mole) of anhydrous NaBr for LiCl to yield 6.4 g of $NaBF_3Br$.

Example 3

Synthesis of $KBF_3I$

The procedure of Example 1 is repeated with the substitution of 4.98 g (0.03 mol) of anhydrous KI for LiCl to yield 10.2 g of $NaBF_3Br$.

Example 4

Synthesis of $(C_2H_5)_4NBF_2Br_2$

The procedure of Example 1 is repeated with 40 ml dimethoxyethane and the substitution of 12.6 g (0.06 mol) of $(C_2H_5)_4NBr$ for LiCl to yield 6.6 g of $(C_2H_5)_4NBF_2Br_2$.

Example 5

Synthesis of $LiBFCl_3$

The procedure of Example 1 is repeated with the substitution of 3.53 g (0.03 mol) of $BCl_3$ for $BF_3$; and 0.78 g (0.03 mol) of LiF for LiCl to yield 3.25 g of $LiBFCl_3$.

Example 6

$LiBF_3Cl$ Electrolytic Solution

In a glove-box having a moisture level less than 20 ppm, an electrolytic solution of 1.0 mol $LiBF_3Cl$ salt per kilogram solvent is prepared in a 1:1:3 (wt.) mixture of ethylene carbonate (EC), gamma-butyrolactone (GBL), and ethylmethyl carbonate (EMC). Ionic conductivities of the solution at various temperatures are measured and listed in Table 1.

TABLE 1

Ionic conductivity of 1.0 m LiBF$_3$Cl
1:1:3 EC/GBL/EMC solution

| T/° C. | σ/mS cm$^{-1}$ | T/° C. | σ/mS cm$^{-1}$ |
|---|---|---|---|
| −50 | 0.33 | 10 | 2.59 |
| −40 | 0.56 | 20 | 3.10 |
| −30 | 0.86 | 30 | 3.56 |
| −20 | 1.21 | 40 | 4.02 |
| −10 | 1.58 | 50 | 4.50 |
| 0 | 1.98 | 60 | 4.97 |

Cyclic voltammetry is used to test cycling ability of lithium metal in the solution. Results show that lithium is reversibly plated and striped on the surface of copper in the solution, and that cycling efficiency remained constant with the cycling number.

Figure 2:
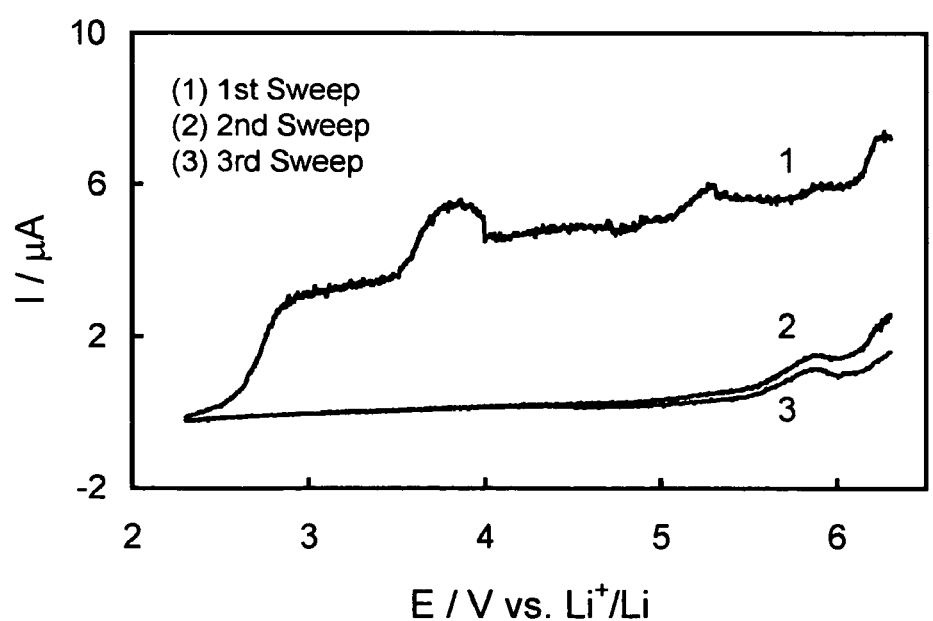
FIG. 2 is a plot showing aluminum electrochemical passivation in 1.0 M $LiBF_3Cl$ dissolved in 1:1:3 (by volume) ethylene carbonate/gamma-butyrolactone/ethylmethyl carbonate solution, recorded at a sweep rate of 5 mV/s.

A freshly scratched Al wire having a 0.1 cm diameter is used as the working electrode to determine anodic ability of the electrolyte. FIG. 2 shows current response with respect to the potential. In the first sweep, the current is increased initially with the potential but immediately suppressed, and in the following sweeps the current is low. These results indicate that the inventive electrolyte passivates Al well at high potentials and the salt is electrochemically stable against high potentials. A small, broad peak of anodic currents at from 5 to 6 V vs. Li$^+$/Li is noted that is associated with mild oxidization of chloride in the LiBF$_3$Cl salt.

Example 7

LiBF$_3$Cl Electrolyte Operation in Li/Graphite Cell

Figure 3:
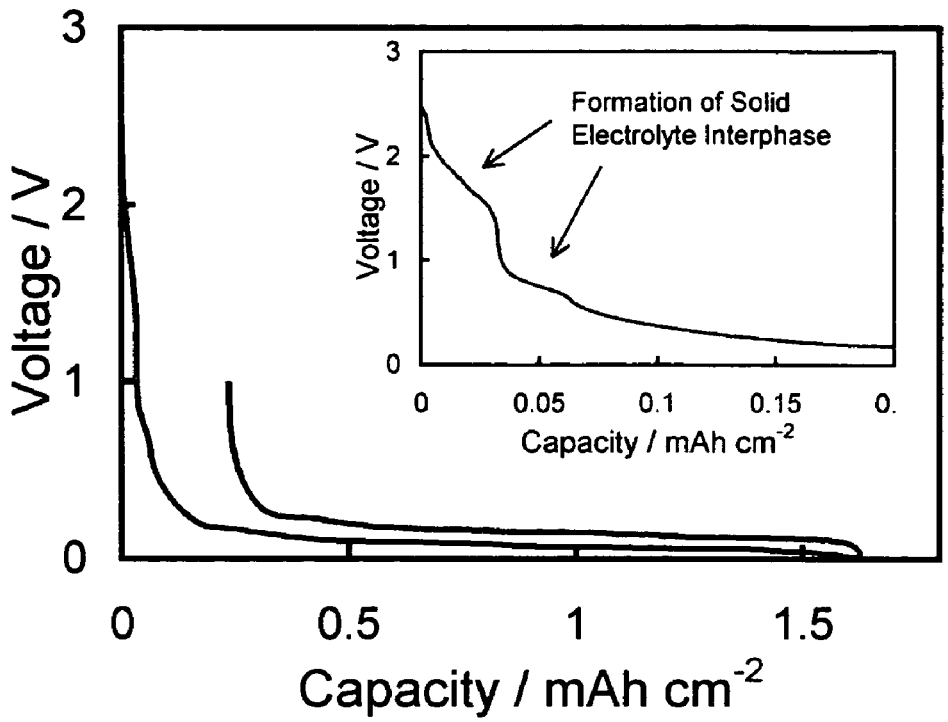
FIG. 3 is a plot showing reversible intercalation and deintercalation of $Li^+$ ions with natural graphite, recorded from the first cycle of a Li/graphite cell using the electrolyte described with respect to FIG. 2.

In a glove-box having a moisture level less than 20 ppm, a Li/graphite cell is assembled using the solution prepared in Example 6 as the electrolyte. The cell is cycled at a constant current rate of 0.1 C by discharging the cell from open circuit voltage to 0.002 V and then charging the cell to 1.5 V. FIG. 3 shows a plot of the cell voltage versus capacity in the first cycle. It is noted that the cell voltage first passes two short plateaus from open circuit voltage to 0.5 V (as shown in inset), and then displays long plateaus with an increase in the capacity. The latter plateaus reversibly return as the cell is charged. This feature is a characteristic of lithium ions intercalating and deintercalating with graphite. Cycling efficiency of the first cycle is 85% and increased to nearly 100% and remained stable in the further cycles. The results above indicate that with the electrolyte, a protective solid electrolyte interphase forms on the surface of graphite, and lithium ions are reversibly cycled with graphite.

Example 8

LiBF$_3$Cl Electrolyte Operation in a Li/LiNi$_{0.8}$Co$_{0.2}$O$_2$ Cell

Figure 4:
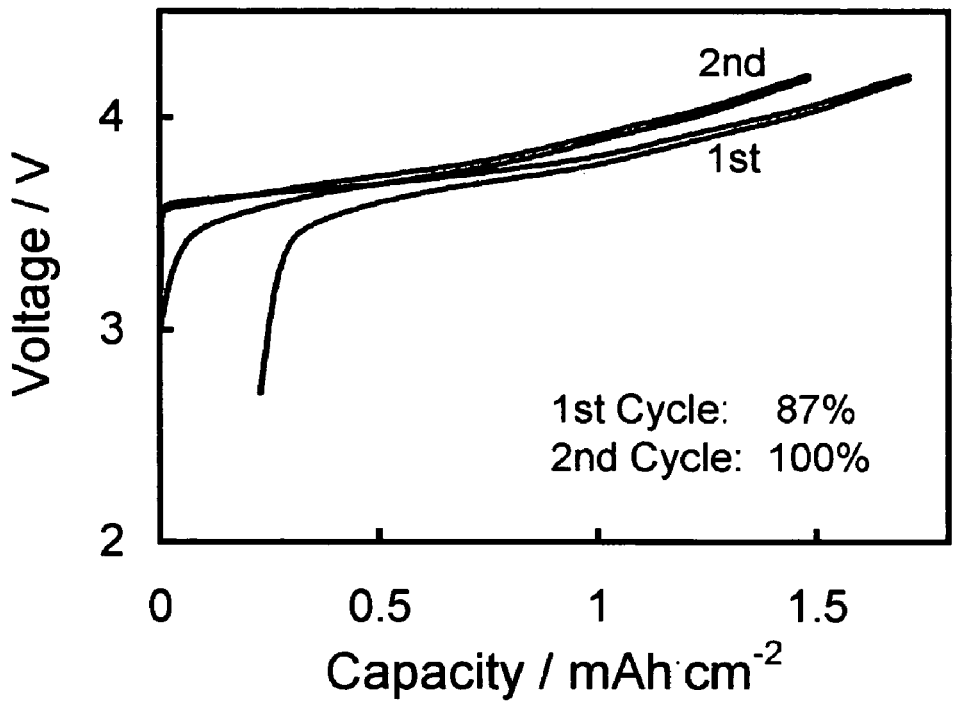
FIG. 4 is a plot showing reversible deintercalation and intercalation of $Li^+$ ions in $LiNi_{0.8}Co_{0.2}O_2$ cathode recorded from the initial two cycles of a $Li/LiNi_{0.8}Co_{0.2}O_2$ cell using the electrolyte described with respect to FIG. 2.

Using the electrolyte described in Example 2, a Li/LiNi$_{0.8}$Co$_{0.2}$O$_2$ cell is assembled in a nitrogen atmosphere, <20 ppm water glove-box. The cell is cycled at a constant current rate of 0.1 C between 2.5 V and 4.2 V. FIG. 4 shows plots of the cell voltage versus capacitance for the initial two cycles. The cycling efficiency in the first cycle is 87% and increases to 100% in the second cycle. It is known that the relatively low reversibility of the first cycle is due to an irreversible change in the crystallographic structure of LiNiO$_2$-based cathode materials. These cell voltage plots indicate that the electrolyte made of LiBF$_3$Cl salt is suitable for rechargeable lithium batteries.

Example 9

LiBF$_3$Cl Electrolyte Operation in a Graphite/ LiNi$_{0.8}$Co$_{0.2}$O$_2$ cell.

Figure 5:
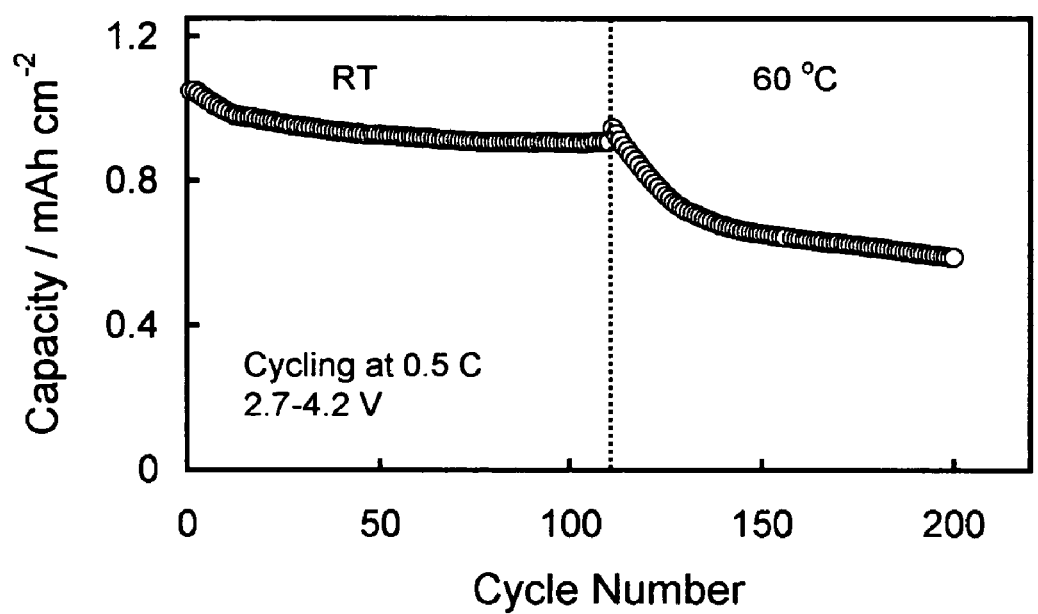
FIG. 5 is a plot showing discharge capacities of a graphite/ $LiNi_{0.8}Co_{0.2}O_2$ Li-ion cell using the same electrolyte described with respect to FIG. 2.

Using the same materials described above in Examples 7 and 8, a graphite/LiNi$_{0.8}$Co$_{0.2}$O$_2$ cell is assembled and cycled at 0.5 C between 2.5 V and 4.1 V. FIG. 5 shows discharge capacities of the cell at room temperature and at 60° C., respectively. It indicates that LiBF$_3$C1-based electrolytes are suitable for use in Li-ion batteries.

Patent documents and publications mentioned in the specification are indicative of the levels of those skilled in the art to which the invention pertains. These documents and publications are incorporated herein by reference to the same extent as if each individual document or publication was specifically and individually incorporated herein by reference.

The foregoing description is illustrative of particular embodiments of the invention, but is not meant to be a limitation upon the practice thereof. The following claims, including all equivalents thereof, are intended to define the scope of the invention.

The invention claimed is:

1. A composition comprising:

$$MBF_{4-n}X_n \qquad (I)$$

where M is R$_1$R$_2$R$_3$R$_4$N$^+$, or an alkali metal cation lithium, sodium, potassium or cesium;
n is an integer 1, 2, or 3; X is a halide chloride, bromide or iodide; and each of R$_1$, R$_2$, R$_3$ and R$_4$ is independently a C$_1$-C$_8$ alkyl.

2. The composition of claim 1 wherein M is lithium.

3. The composition of claim 2 wherein X is chloride.

4. The composition of claim 2 wherein X is bromide.

5. The composition of claim 2 wherein X is iodide.

6. The composition of claim 1 wherein M is sodium.

7. A process for forming an alkali metal or quaternary ammonium fluorohaloborate comprising:

suspending MX in an aprotic solvent where M is R$_1$R$_2$R$_3$R$_4$N$^+$ or an alkali metal cation of lithium, sodium, potassium or cesium; X is a halide chloride, bromide or iodide; and each of R$_1$, R$_2$, R$_3$ and R$_4$ is independently C$_1$-C$_8$ alkyl;
reacting MX with a BF$_3$ organic adduct complex in said aprotic solvent to form MBF$_{4-n}$X$_n$ where n is 1, 2 or 3; and
collecting MBF$_{4-n}$X$_n$ as a solid from said aprotic solvent.

8. The process of claim 7 wherein said BF$_3$ organic adduct complex is BF$_3$ etherate.

9. The process of claim 7 wherein said BF$_3$ organic adduct complex is in a volume ratio to said solvent of 1:1-20.

10. The process of claim 7 wherein said BF$_3$ organic adduct complex is in a volume ratio to said solvent of 1:1-10.

11. The process of claim 7 wherein said solvent is selected from the group consisting of: dimethylcarbonate (C$_1$-C$_6$ alkyl)-OC(O)—O—(C$_1$-C$_6$ alkyl), a C$_2$-C$_8$ alkaline carbonate, a C$_1$-C$_6$ dialkoxy of a C$_2$-C$_6$ alkane, a C$_1$-C$_6$ ester of a C$_2$-C$_8$ carboxylic acid, a C$_1$-C$_6$ alkyl tetrahydrofuran and mixtures thereof.

12. A process for forming an alkali metal or quaternary ammonium fluorohaloborate comprising:

suspending MF in an aprotic solvent where M is $R_1R_2R_3R_4N^+$ or an alkali metal cation of lithium, sodium, potassium or cesium; and each of $R_1$, $R_2$, $R_3$ and $R_4$ is independently $C_1$-$C_8$ alkyl;

reacting MF with a $BX_3$ organic adduct complex in said aprotic solvent to form $MBFX_3$ where X is a halide chloride, bromide or iodide; and collecting $MBFX_3$ as a solid from said aprotic solvent.

13. The process of claim 12 wherein said solvent is selected from the group consisting of: dimethylcarbonate ($C_1$-$C_6$ alkyl)-OC(O)—O—($C_1$-$C_6$ alkyl), a $C_2$-$C_8$ alkaline carbonate, a $C_1$-$C_6$ dialkoxy of a $C_2$-$C_6$ alkane, a $C_1$-$C_6$ ester of a $C_2$-$C_8$ carboxylic acid, a $C_1$-$C_6$ alkyl tetrahydrofuran and mixtures thereof.

14. The process of claim 12 wherein said $BX_3$ complex and said MF are present in a molar ratio of from 0.8 to 1.2 inclusive.

15. An electrolyte comprising a composition of claim 1 and a solvent mixture containing at least one solvent selected from the group consisting of: dimethylcarbonate, ($C_1$-$C_6$ alkyl)-OC(O)—O—($C_1$-$C_6$ alkyl), a $C_2$-$C_8$ alkaline carbonate, a $C_1$-$C_6$ dialkoxy of a $C_2$-$C_6$ alkane, a $C_1$-$C_6$ ester of a $C_2$-$C_8$ carboxylic acid, a $C_1$-$C_6$ dialkyl sulfoxide, dioxolane, sulfolane, pyrrolidinones, lactones, acetonitrile, tetrahydrofuran, $C_1$-$C_6$ alkyl tetrahydrofurans and mixtures thereof.

16. The electrolyte of claim 15 wherein said compound is present from 0.01-3 mols per liter of said solvent mixture.

17. The electrolyte of claim 15 wherein said solvent mixture has at least one alkaline carbonate.

18. The electrolyte of claim 15 wherein said solvent mixture has at least one ($C_1$-$C_6$ alkyl)-OC(O)—O—($C_1$-$C_6$ alkyl).

19. The electrolyte of claim 15 wherein said solvent mixture has at least one lactone.

20. The electrolyte of claim 15 wherein said solvent mixture includes an alkaline carbonate in a weight ratio to ($C_1$-$C_6$ alkyl)-OC(O)—O—($C_1$-$C_6$ alkyl) of from 0.1 to 10:1.

21. An electrochemical device comprising:
a cathodic electrode;
an anodic electrode; and
an electrolyte according to claim 15.

22. The electrochemical device of claim 21 wherein said cathodic electrode is carbon and said anodic electrode is carbon.

\* \* \* \* \*